United States Patent [19]

Carrera et al.

[11] Patent Number: 5,840,505
[45] Date of Patent: Nov. 24, 1998

[54] METHOD FOR INHIBITING ADENYLOSUCCINATE SYNTHETASE ACTIVITY IN METHYLTHIOADENOSINE PHOSPHORYLASE DEFICIENT CELLS

[75] Inventors: Carlos J. Carrera, San Diego; Dennis A. Carson, Del Mar; Howard B. Cottam, Fallbrook; Tsutomu Nobori, San Diego, all of Calif.

[73] Assignee: The Regents of the University of California, Oakland, Calif.

[21] Appl. No.: 612,542

[22] Filed: Mar. 8, 1996

Related U.S. Application Data

[63] Continuation-in-part of Ser. No. 176,855, Dec. 29, 1993, abandoned.

[51] Int. Cl.[6] .............................. C12Q 1/34; C12Q 1/46; C12Q 1/48; C12Q 1/37
[52] U.S. Cl. ............................... 435/18; 435/21; 435/15; 435/24; 435/23; 435/4; 435/69.2; 435/68.1; 435/975; 435/963; 435/172.2; 435/968; 435/29; 536/24.32; 536/24.31; 514/45
[58] Field of Search .................................. 435/18, 21, 15, 435/24, 23, 4, 69.2, 68.1, 975, 963, 172.2, 968, 29; 536/24.32, 24.31; 514/45

[56] References Cited

U.S. PATENT DOCUMENTS

| | | | |
|---|---|---|---|
| 4,792,520 | 12/1988 | Stambrook et al. | 435/6 |
| 4,822,736 | 4/1989 | Kellems et al. | 435/91 |
| 5,030,623 | 7/1991 | Gruber | 514/45 |
| 5,118,601 | 6/1992 | Gruber | 435/29 |

OTHER PUBLICATIONS

Willis et al; Adv. Exp. Med. Biol.; vol. 122B, pp. 237–241; 1980.

Guicherit et al; J. Biol. Chem; vol. 269, No. 6, pp. 4488–4496, 1994.

*Primary Examiner*—Louise N. Leary
*Attorney, Agent, or Firm*—Fish & Richardson P.C.

[57] ABSTRACT

An in vivo method for depleting mammalian cells of adenosine 5'-monophosphate (AMP) useful in the treatment of certain cancers is provided. According to the method, a population of cells is obtained from a host and assayed for loss of methylthioadenosine phosphorylase (MTAse) activity. MTAse catabolizes methylthioadenosine to adenine for endogenous salvage incorporation into the intracellular AMP pool. The preferred method for assaying loss of MTAse activity is a hybridization technique for detection of a homozygous loss of the gene which encodes MTAse. Hosts having MTAse deficient tumors are treated with a therapeutically effective amount of an agent which inhibits the activity of adenylsuccinate synthetase, which converts inosine 5'-monophosphate to AMP, thus depleting the tumor cells of substrates for de novo AMP production. L-alanosine is the preferred ASS inhibitory agent for use in the method of the invention.

13 Claims, 6 Drawing Sheets

| | | | | | |
|---|---|---|---|---|---|
| 1 | TTTATACAGA | GCATGACAGT | GGGGTCCTCA | CTAGGGTCTG | TCTGCCACTC |
| 51 | TACATATTTG | AAACAGGAGT | GGCTTCTCAG | AATCCAGTGA | ACCTAAATTT |
| 101 | TAGTTTTAGT | TGCTCACTGG | ACTGGGTTCT | AGGAGACCCC | CTGTGTTAGT |
| 151 | CTGTGGTCAT | TGCTAGSAGA | ATCACTTAAT | TTTTTCTAGA | CTCTAGGAGA |
| 201 | AAACAGTTGG | TGGTGTACTC | ATCACGGGTT | AACAATTTCT | TCTCTCCTTC |
| 251 | CATAGGCATG | GAAGGCAGCA | CACCATCATG | CCTTCAAAGG | TCAACTACCA |
| 301 | GGCGAACATC | TGGGCTTTGA | AGGAAGAGGG | CTGTACACAT | GTCATAGTGA |
| 351 | CCACAGCTTG | TGGCTCCTTG | AGGGAGGAGA | TTCAGCCCGG | CGATATTGTC |
| 401 | ATTATTGATC | AGTTCATTGA | CANNNNNNNN | NNNNNNNNNN | GAGGTCGACG |
| 451 | GTATCGATAA | GCTTTGTAAA | CAATTGTCTT | TAGCTTATCC | AGAGGAATTG |
| 501 | AGTCTGGAGT | AAAGACCCAA | ATATTGACCT | AGATAAAGTT | GACTCACCAG |
| 551 | CCCTCGGAGG | ATGGAAAGAT | GGCCTTAAAA | TAAAACAAAC | AAAAACCTTT |
| 601 | TTTGCTTTAT | TTTGTAGGAC | CACTATGAGA | CCTCAGTCCT | TCTATGATGG |
| 651 | AAGTCATTCT | TGTGCCAGAG | GAGTGTGCCA | TATTCCAATG | GCTGAGCCGT |
| 701 | TTTGCCCCAA | AACGAGAGAG | GTGTGTAGTC | TTTCTGGAAG | GTGTACCAGA |
| 751 | ATAAATCATG | TGGGCTTGGG | GTGGCATCTG | GCATTTGGTT | AATTGGCAGA |
| 801 | CGGAGTGGCC | CCATACCCTC | ACTCAAGTTT | GCTTTGTATT | ATGCAAGTTT |
| 851 | ATGGAGAGTT | ATTTCCTGTT | GCTAATAATT | TNNNNNNNNN | NNNNNNNNNN |
| 901 | AAGTGCAGCC | TTAAGTTGTG | CATGTGCTAG | TATGTTTTGA | AGTTTCTGGT |
| 951 | TTTTCTTTTC | TAGGTTCTTA | TAGAGACTGC | TAAGAAGCTA | GGACTCCGGT |
| 1001 | GCCACTCAAA | GGGGACAATG | GTCACAATCG | AGGGACCTCG | TTTTAGCTCC |
| 1051 | CGGGCAGAAA | GCTTCATGTT | CCGCACCTGG | GGGGCGGATG | TTATCAACAT |
| 1101 | GACCACAGTT | CCAGAGGTGG | TTCTTGCTAA | GGAGGCTGGA | ATTTGTTACG |
| 1151 | CAAGTATCGC | CATGGGCACA | GATTATGACT | GCTGGAAGGA | GCACGAGGAA |
| 1201 | GCAGTAGGTG | GAATTCTTTT | CTAAGCACAT | ATAGCATGGG | TTTCTGGGTG |
| 1251 | CCAATAGGGT | GTCTTAACTG | TTTGTTTCTA | TTACGTTAGT | TTCAGAAAGT |
| 1301 | GCCTTTCTAC | AAGGTTTTGA | AGTTGTTAAT | ATTTTCTGTA | GTTCCATTGG |
| 1351 | AAGGTAAGAA | CAAAGATCAA | AAGAAAGAAA | GAGACACTTT | TACCCAAGGA |
| 1401 | TCAGTAGTGA | AAATAGTACA | TTGTAGGCAT | GTAGATGTGT | TGAGAATCAT |

| | | | | | |
|---|---|---|---|---|---|
| 1 | TTTATACAGA | GCATGACAGT | GGGGTCCTCA | CTAGGGTCTG | TCTGCCACTC |
| 51 | TACATATTTG | AAACAGGAGT | GGCTTCTCAG | AATCCAGTGA | ACCTAAATTT |
| 101 | TAGTTTTAGT | TGCTCACTGG | ACTGGGTTCT | AGGAGACCCC | CTGTGTTAGT |
| 151 | CTGTGGTCAT | TGCTAGSAGA | ATCACTTAAT | TTTTTCTAGA | CTCTAGGAGA |
| 201 | AAACAGTTGG | TGGTGTACTC | ATCACGGGTT | AACAATTTCT | TCTCTCCTTC |
| 251 | CATAGGCATG | GAAGGCAGCA | CACCATCATG | CCTTCAAAGG | TCAACTACCA |
| 301 | GGCGAACATC | TGGGCTTTGA | AGGAAGAGGG | CTGTACACAT | GTCATAGTGA |
| 351 | CCACAGCTTG | TGGCTCCTTG | AGGGAGGAGA | TTCAGCCCGG | CGATATTGTC |
| 401 | ATTATTGATC | AGTTCATTGA | CANNNNNNNN | NNNNNNNNNN | GAGGTCGACG |
| 451 | GTATCGATAA | GCTTTGTAAA | CAATTGTCTT | TAGCTTATCC | AGAGGAATTG |
| 501 | AGTCTGGAGT | AAAGACCCAA | ATATTGACCT | AGATAAAGTT | GACTCACCAG |
| 551 | CCCTCGGAGG | ATGGAAAGAT | GGCCTTAAAA | TAAAACAAAC | AAAAACCTTT |
| 601 | TTTGCTTTAT | TTTGTAGGAC | CACTATGAGA | CCTCAGTCCT | TCTATGATGG |
| 651 | AAGTCATTCT | TGTGCCAGAG | GAGTGTGCCA | TATTCCAATG | GCTGAGCCGT |
| 701 | TTTGCCCCAA | AACGAGAGAG | GTGTGTAGTC | TTTCTGGAAG | GTGTACCAGA |
| 751 | ATAAATCATG | TGGGCTTGGG | GTGGCATCTG | GCATTTGGTT | AATTGGCAGA |
| 801 | CGGAGTGGCC | CCATACCCTC | ACTCAAGTTT | GCTTTGTATT | ATGCAAGTTT |
| 851 | ATGGAGAGTT | ATTTCCTGTT | GCTAATAATT | TNNNNNNNNN | NNNNNNNNNN |
| 901 | AAGTGCAGCC | TTAAGTTGTG | CATGTGCTAG | TATGTTTTGA | AGTTTCTGGT |
| 951 | TTTTCTTTTC | TAGGTTCTTA | TAGAGACTGC | TAAGAAGCTA | GGACTCCGGT |
| 1001 | GCCACTCAAA | GGGGACAATG | GTCACAATCG | AGGGACCTCG | TTTTAGCTCC |
| 1051 | CGGGCAGAAA | GCTTCATGTT | CCGCACCTGG | GGGGCGGATG | TTATCAACAT |
| 1101 | GACCACAGTT | CCAGAGGTGG | TTCTTGCTAA | GGAGGCTGGA | ATTTGTTACG |
| 1151 | CAAGTATCGC | CATGGGCACA | GATTATGACT | GCTGGAAGGA | GCACGAGGAA |
| 1201 | GCAGTAGGTG | GAATTCTTTT | CTAAGCACAT | ATAGCATGGG | TTTCTGGGTG |
| 1251 | CCAATAGGGT | GTCTTAACTG | TTTGTTTCTA | TTACGTTAGT | TTCAGAAAGT |
| 1301 | GCCTTTCTAC | AAGGTTTTGA | AGTTGTTAAT | ATTTTCTGTA | GTTCCATTGG |
| 1351 | AAGGTAAGAA | CAAAGATCAA | AAGAAAGAAA | GAGACACTTT | TACCCAAGGA |
| 1401 | TCAGTAGTGA | AAATAGTACA | TTGTAGGCAT | GTAGATGTGT | TGAGAATCAT |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 2763 base pairs
        ( B ) TYPE: nucleic acid
        ( C ) STRANDEDNESS: single
        ( D ) TOPOLOGY: linear     ( i i ) MOLECULE TYPE: DNA (genomic)

( v i i ) IMMEDIATE SOURCE:
        ( B ) CLONE: methyladenosine phosphatase     ( i x ) FEATURE:
        ( A ) NAME/KEY: CDS
        ( B ) LOCATION: 1..2763

( x i ) SEQUENCE DESCRIPTION: SEQ ID NO:1:

```
TTTATACAGA  GCATGACAGT  GGGGTCCTCA  CTAGGGTCTG  TCTGCCACTC  TACATATTTG    60

AAACAGGAGT  GGCTTCTCAG  AATCCAGTGA  ACCTAAATTT  TAGTTTTAGT  TGCTCACTGG   120

ACTGGGTTCT  AGGAGACCCC  CTGTGTTAGT  CTGTGGTCAT  TGCTAGSAGA  ATCACTTAAT   180

TTTTTCTAGA  CTCTAGGAGA  AAACAGTTGG  TGGTGTACTC  ATCACGGGTT  AACAATTTCT   240

TCTCTCCTTC  CATAGGCATG  GAAGGCAGCA  CACCATCATG  CCTTCAAAGG  TCAACTACCA   300

GGCGAACATC  TGGGCTTTGA  AGGAAGAGGG  CTGTACACAT  GTCATAGTGA  CCACAGCTTG   360

TGGCTCCTTG  AGGGAGGAGA  TTCAGCCCGG  CGATATTGTC  ATTATTGATC  AGTTCATTGA   420

CANNNNNNNN  NNNNNNNNNN  GAGGTCGACG  GTATCGATAA  GCTTTGTAAA  CAATTGTCTT   480

TAGCTTATCC  AGAGGAATTG  AGTCTGGAGT  AAAGACCCAA  ATATTGACCT  AGATAAAGTT   540

GACTCACCAG  CCCTCGGAGG  ATGGAAAGAT  GGCCTTAAAA  TAAAACAAAC  AAAAACCTTT   600

TTTGCTTTAT  TTTGTAGGAC  CACTATGAGA  CCTCAGTCCT  TCTATGATGG  AAGTCATTCT   660

TGTGCCAGAG  GAGTGTGCCA  TATTCCAATG  GCTGAGCCGT  TTTGCCCCAA  AACGAGAGAG   720

GTGTGTAGTC  TTTCTGGAAG  GTGTACCAGA  ATAAATCATG  TGGGCTTGGG  GTGGCATCTG   780

GCATTTGGTT  AATTGGCAGA  CGGAGTGGCC  CCATACCCTC  ACTCAAGTTT  GCTTTGTATT   840

ATGCAAGTTT  ATGGAGAGTT  ATTTCCTGTT  GCTAATAATT  TNNNNNNNNN  NNNNNNNNNN   900

AAGTGCAGCC  TTAAGTTGTG  CATGTGCTAG  TATGTTTTGA  AGTTTCTGGT  TTTTCTTTTC   960

TAGGTTCTTA  TAGAGACTGC  TAAGAAGCTA  GGACTCCGGT  GCCACTCAAA  GGGGACAATG  1020

GTCACAATCG  AGGGACCTCG  TTTTAGCTCC  CGGGCAGAAA  GCTTCATGTT  CCGCACCTGG  1080

GGGGCGGATG  TTATCAACAT  GACCACAGTT  CCAGAGGTGG  TTCTTGCTAA  GGAGGCTGGA  1140

ATTTGTTACG  CAAGTATCGC  CATGGGCACA  GATTATGACT  GCTGGAAGGA  GCACGAGGAA  1200
```

```
GCAGTAGGTG  GAATTCTTTT  CTAAGCACAT  ATAGCATGGG  TTTCTGGGTG  CCAATAGGGT   1260

GTCTTAACTG  TTTGTTTCTA  TTACGTTAGT  TTCAGAAAGT  GCCTTTCTAC  AAGGTTTTGA   1320

AGTTGTTAAT  ATTTCTGTA   GTTCCATTGG  AAGGTAAGAA  CAAAGATCAA  AAGAAAGAAA   1380

GAGACACTTT  TACCCAAGGA  TCAGTAGTGA  AAATAGTACA  TTGTAGGCAT  GTAGATGTGT   1440

TGAGAATCAT  ACTAAGACTT  GGGCCTTANN  NNNNNNNNNN  NNNNNNNNNN  NNTACCCTAC   1500

ATTGAGGATT  CGGTTTCAGC  AGATAAATTT  GAGGGACACA  AACATTTAGG  CTGTAGCAAG   1560

GCTGGAGCTC  AGAAAAATGT  TTTATGACAA  GCAGTGGAAT  TTTAAGTTCT  AGTAACCTCC   1620

AGTGCTATTG  TTTCTCTAGG  TTTCGGTGGA  CCGGGTCTTA  AAGACCCTGA  AAGAAAACGC   1680

TAATAAAGCC  AAAAGCTTAC  TGCTCACTAC  CATACCTCAG  ATAGGGTCCA  CAGAATGGTC   1740

AGAAACCCTC  CATAACCTGA  AGGTAAGTGC  AGCCATGGAC  AATCAGGCAT  GTCTGTAGAC   1800

TCTCTATTGT  CTTCTTTTCT  TACTTGCATT  TCACCTTTGG  TCCTCATGTA  TTTTTTGCCA   1860

GCCTAGATGT  TTTCAACAAG  TTTTTGTGAC  ATCTACTACT  ACCATACCAA  CCACTTGTGA   1920

AACTGAGTAG  TCTTATTTTC  TTGGCTGGTA  GTGCAGANNN  NNNNNNNNNN  NNAATAAACA   1980

ATAATCCAGG  CTGGGCTGGT  ATGGCAATAA  GTGATTATCA  GAACAATGCT  CTGAGATAAG   2040

CATTATTAAC  CTCACTTTAC  AGGAAAGGGA  GGTGAGGAAC  CAAGAGTTTA  GAGTACCCGA   2100

AGTTCCACAT  CTGGTTAGTG  AACTTGAAAA  TTTTCTGTAG  AATTTATTTA  AAGTGTATGT   2160

TTCCTGCGTC  CTCACTTTGA  TCTAGAAAAT  CAAAATCTGT  TTTTTTTTT   AACAAACATC   2220

TCAGTAATTA  CGCCAACATG  TGAATATCAC  TGCCTCCTTT  CTTCCTTTCA  GAATATGGCC   2280

CAGTTTTCTG  TTTTATTACC  AAGACATTAA  AGTAGCATGG  CTGCCCAGGA  GAAAAGAAGA   2340

CATTCTAATT  CCAGTCATTT  TGGGAATTCC  TGCTTAACTT  GAAAAAAATA  TGGGAAAGAC   2400

ATGCAGCTTT  CATGCCCTTG  CCTATCAAAG  AGTATGTTGT  AAGAAAGACA  AGACATTGTG   2460

TGTATAGAGA  CTCCTCAATG  ATTTAGACAA  CTTCAAAATA  CAGAAGAAAA  GCAAATGACT   2520

AGTAACATGT  GGGAAAAAAT  ATTACATTTT  AAGGGGGAAA  AAAAACCCCA  CCATTCTCTT   2580

CTCCCCCTAT  TAAATTTGCA  ACAATAAAGG  GTGGAGGGTA  ATCTCTACTT  TCCTATACTG   2640

CCAAAGAATG  TGAGGAAGAA  ATGGGACTCT  TTGGTTATTT  ATTGATGCGA  CTGTAAATTG   2700

GTACAGTATT  TCTGGAGGGC  AATTTGGTAA  AATGCATCAA  AAGACTTAAA  AATACGGACG   2760

TAC                                                                     2763
```

METHOD FOR INHIBITING ADENYLOSUCCINATE SYNTHETASE ACTIVITY IN METHYLTHIOADENOSINE PHOSPHORYLASE DEFICIENT CELLS

CROSS REFERENCE TO RELATED APPLICATIONS

This is a continuation-in-part of U.S. patent application Ser. No. 08/176,855, filed Dec. 29, 1993, now abandoned.

BACKGROUND OF THE INVENTION

The invention relates to pharmaceutical agents and methods for use in chemotherapeutic treatment of cancer. More specifically, the invention relates to the identification of cancer cells which cannot metabolize methylthioadenosine phosphorylase to adenine for the salvage synthesis of adenine nucleotides, and the use of L-alanosine to inhibit de novo adenosine 5'-monophosphate (AMP) synthesis in such cancer cells.

HISTORY OF THE INVENTION

Methylthioadenosine (MTA) is cleaved in healthy mammalian cells by methylthioadenosine phophorylase (MTAse) into adenine and methylthioribose-1-P, the latter of which is a substrate for metabolic synthesis of methionine. Adenine is salvaged into a cellular pool of adenosine 5'-monophosphate (AMP), from which cells derive adenosine 5'-triphosphate (ATP) for metabolic energy and 2'-deoxyadenosine-5'-triphosphate (dATP) for DNA synthesis.

Based on early in vitro studies, the L isomer of a bacterial antibiotic alanosine (obtained from Streptomyces alanosinicus; hereafter, "L-alanosine") appeared to have promise for use as an anti-viral and anti-tumor agent. In particular, it is believed that L-alanosine inhibits adenylosuccinate synthetase (ASS) conversion of inosine 5'-monophosphate (IMP) to AMP, thus depleting target cells of AMP and ATP (in the absence of adenine). However, clinical studies of the therapeutic efficacy of L-alanosine in human cancer patients have been disappointing (see, e.g., data collected in Tyagi and Cooney, *Adv. Pharmacol. Chemotherapy*, 20:69–120, 1984 [results then to date offered "little encouragement" regarding L-alanosine's efficacy for treatment of human cancers]; Creagan, et al., *Cancer*, 52:615–618, 1993 [Phase II studies had overall response rate of only 4%]; Creagan, et al., *Am.J.Clin.Oncol.*, 7:543–544, 1984 [Phase II study in melanoma patients; little therapeutic response observed]; VonHoff, et al., *Invest. New Drugs*, 9:87–88, 1991 [no objective responses observed in breast cancer patients]). Eventually, all clinical trials of L-alanosine for use in treatment of cancer were abandoned.

Another known inhibitor of ASS activity is hadacidin. However, hadacidin is believed to be more toxic than L-alanosine in humans. Further, the activity of other inhibitors of de novo purine synthesis (such as methotrexate, 6-mercaptopurine, 6-thioguanine and dideazatetrahydrofolate) which block IMP synthesis (and therefore theoretically eliminate IMP as a source for AMP production) has been circumvented in vivo by salvage of hypoxanthine, which is abundant in plasma, for use as a substrate for IMP production. Hence, to date the in vivo performance of agents which block the adenine metabolic pathway for intracellular AMP production has been frustratingly poor.

However, with the development of an assay of sufficient sensitivity to identify homozygous deletions of the gene encoding MTAse in certain human cancer cells (see, commonly assigned parent U.S. patent application Ser. No. 08/176,855), it now appears that the tumors treated in the clinical trials of L-alanosine produced MTAse and were therefore able to provide sufficient adenine to maintain a pool of AMP despite inhibition of AMP production from IMP. The present invention therefore provides a method for identifying cells which lack MTAse and for treating such cells by depleting them of AMP.

SUMMARY OF THE INVENTION

It has been discovered that cells from which the gene which encodes MTAse protein has been deleted and are therefore not able to metabolize MTA to adenine ("MTAse deficient cells") are selectively killed in vivo on contact with therapeutically effective dosages of a de novo AMP synthesis inhibitor such as L-alanosine. Thus, while L-alanosine is not therapeutically effective against all cancer cells, it is therapeutically effective against MTAse deficient cells.

In one aspect, the invention provides a method for determining whether particular cancer cells are MTAse deficient by providing assays to determine whether the cells lack MTAse protein. The preferred assay for use in this regard is one for detection of homozygous deletions from cells of the gene which encodes MTAse protein.

In another aspect, the invention provides a method for treating MTAse deficient cancers by contacting MTAse deficient cells with a therapeutically effective amount of a de novo purine synthesis inhibitor which inhibits the activity of ASS, preferably L-alanosine. The ASS inhibitory agents of the invention may be administered by any clinically acceptable means, but are preferably administered by continuous infusion at concentrations below the maximally tolerated dose to prolong the desired inhibitory activity and minimize toxicity to host tissues.

Also provided are kits for use in the methods of the invention which include reagents for use in performing the MTAse deficiency assay of the invention as well as pharmaceutical compositions of an ASS inhibitor, preferably L-alanosine and/or its active metabolite, L-alanosinyl AICOR.

BRIEF DESCRIPTION OF THE DRAWINGS

FIG. 1 is a partial nucleotide sequence for genomic MTAse (SEQ.ID.No.1) wherein the exons are underlined.

FIGS. 4 and 5 (A–B) are graphs depicting the effect of administering various exogenous MTAse substrates to MTAse competent or MTAse deficient cell lines after treatment with L-alanosine.

DESCRIPTION OF THE PREFERRED EMBODIMENTS

I. METABOLIC PATHWAYS FOR INTRACELLULAR PRODUCTION OF AMP

Figure 6:
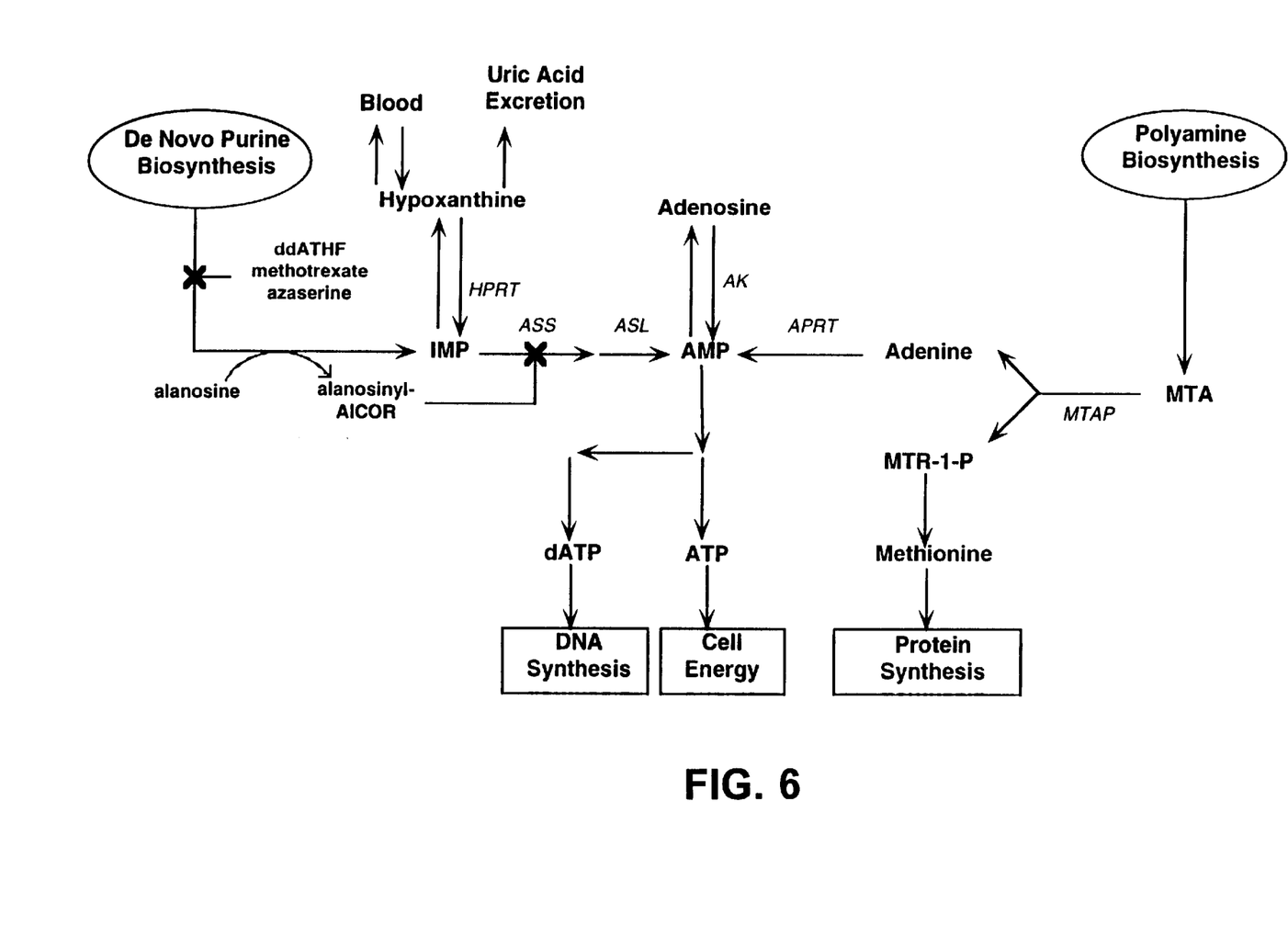
FIG. 6 is a schematic depiction of the intracellular metabolic pathways for production of AMP.

To assist in understanding the invention, a chart depicting the intracellular metabolic pathways by which AMP is produced is provided in FIG. 6. In summary, there are three principal sources of substrates for intracellular AMP production. The first is catabolism of methylthioadenosine to adenine by MTAse. This pathway is blocked in MTAse deficient cells.

The second is conversion of IMP to AMP by the activity of ASS or adenylsuccinate lyase (ASL). There are presently no known inhibitors of ASL activity. However, with loss of ASS activity, IMP→RAMP conversion is substantially eliminated.

The third is hypoxanthine salvage to AMP. However, because IMP→RAMP conversion occurs distal to hypoxanthine salvage, inhibition of ASS catabolism of IMP→AMP blocks the hypoxanthine salvage pathway.

II. METHOD FOR DETERMINING WHETHER TUMOR CELLS IN AN ASSAYABLE SAMPLE OBTAINED FROM A MAMMALIAN HOST ARE MTAse DEFICIENT

A. Polynucleotide Reagents for Use in Identifying MTAse Deficient Cells

The preferred method for determining whether a particular population of cells are MTAse deficient is by hybridization assay to detect homozygous deletions of the gene which encodes MTAse from the cells. Screening procedures which rely on nucleic acid hybridization make it possible to detect any polynucleotide sequence (and, by inference, any protein encoded by such polynucleotide sequence) in any organism, provided the appropriate probe is available.

A complete description of hybridization techniques suitable for use in the invention, as well as a description of the gene which encodes MTAse, are set forth in co-pending, commonly assigned U.S. patent application Ser. No. 08/176,855 (filed Dec. 29, 1993), the disclosure of which is incorporated herein by this reference together with any amendments which may be made thereto. For ease of reference, a partial polynucleotide sequence of the gene which encodes MTAse is described herein at SEQ.ID.No.1 in the appended Sequence Listing and in FIG. 1, where coding regions of the gene are identified by underlining. Genomic MTAse polynucleotide is located on chromosome 9 at region p21. Interestingly, a very high percentage of cells which have a homozygous deletion of the gene which encodes tumor suppressor p16 also have a homozygous deletion of the gene which encodes MTAse. Thus, an alternative means of detecting homozygous deletions of the latter gene (for MTAse) is by detecting a homozygous deletion of the former gene (for p16). For further reference in this regard, see commonly assigned, co-pending U.S. patent application Ser. No. 08/227,800, the disclosure of which is incorporated herein by this reference.

A strain of *E. coli* containing genomic DNA for rat MTAse was deposited with the American Type Culture Collection, Rockville, Md. by mailing before Dec. 29, 1993 and accorded, collectively, Designation Nos. 55536, 55537, 55538, 55539 and 55540. No admission that this deposit is necessary to enable one to practice the invention is made or intended. The deposit will, however, be maintained in viable form for whatever period is or may be required by the patent laws applicable to this disclosure.

To determine whether the MTAse gene has been homozygously deleted from the cells of interest, an assayable sample of cells is obtained from the host. For example, the sample may comprise a body fluid or cells, e.g., from a host tissue or tumor. Such samples are obtained using methods known in the clinical art, e.g., tumor cells may be acquired by biopsy or surgical resection. Preferably, the cells are essentially free from "contaminants"; i.e., cells, proteins and similar components which could falsify the result of the assay. For example, where solid tumors are the source for an assayable cell sample, normal non-malignant cells and the MTAse which may be released from normal cells during the procedure performed to obtain the biological sample would be considered to be contaminants. Such contaminants may be removed by conventional purification techniques; e.g., affinity chromatography with an anti-MTAse antibody.

Because the invention is directed toward detecting the presence or absence of this gene in a sample of cells which are suspected of being MTAse negative, nucleic acids in the sample will preferably be amplified to enhance the sensitivity of the detection method. This amplification is preferably accomplished through the use of the polymerase chain reaction (PCR), although the use of a chain reaction in the polymerization step is not absolutely necessary.

The nucleic acid to be amplified in the sample will consist of genomic or wild-type DNA that would normally be expected to encode MTAse if present in the sample (see, SEQ.ID.No.1). MTAse encoding DNA (hereafter the "target DNA") is believed to be present in all normal mammalian cells, including human cells.

For use as a control or as a source of oligonucleotide probes and primers, genomic MTAse-encoding DNA may be isolated according to methods known in the art such as the method described by Maniatis, et al. in *Molecular Cloning: A Laboratory Manual (Cold Spring Harbor Laboratory*, 1982). A working example demonstrating the isolation of a genomic clone of the human MTAse gene is provided herein wherein a cosmid gene library is screened using an MTAse cDNA oligonucleotide probe (see, Example III). However, those skilled in the art will recognize that other suitable means of obtaining MTAse encoding DNA can be used.

For example, a cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucleotide of interest. Alternatively, a cDNA library can be screened indirectly for expression of peptides of interest (e.g., MTAse protein) having at least one epitope using antibodies specific for the peptides. Such antibodies can be either polyclonally or monoclonally derived and used to detect expression product indicative of the presence of cDNA of interest (see, for further reference, Maniatis, et al., *Molecular Cloning: A Laboratory Manual* (Cold Spring Harbor Lab., New York, 1982).

Polynucleotides for use as controls, probes or primers in the invention can also be synthesized using techniques and nucleic acid synthesis equipment which are well-known in the art. For reference in this regard, see Ausubel, et al., *Current Protocols in Molecular Biology*, Chs. 2 and 4 (Wiley Interscience, 1989).

B. Amplification of MTAse Encoding Genomic DNA and Hybridization Assay Therefor

To enhance the sensitivity of the hybridization assays of the invention, the cell sample to be assayed is preferably subjected to conditions favoring the selective amplification of the target nucleic acid. Preferably, the target nucleic acid will be a polynucleotide portion of the gene which encodes MTAse (i.e., the "target polynucleotide"). The preferred means of amplifying the target polynucleotide is by PCR.

PCR is an in vitro method for the enzymatic synthesis of specific DNA or RNA sequences using oligonucleotide primers that hybridize to specific nucleic acid sequences and flank the region of interest in target nucleic acid. A repetitive series of cycles of template denaturation, primer annealing and enzymatic extension of the annealed primers results in an exponential accumulation of a specific nucleic acid fragment defined at its termini by the 5' ends of the primers. The resulting products (PCR products) synthesized in one cycle act as templates for the next; consequently, the number of target nucleic acid copies approximately doubles in every cycle.

The basic PCR techniques are described in U.S. Pat. Nos. 4,683,195 and 4,683,202 to Mullis, et al., the disclosures of which are incorporated herein as examples of the conventional techniques for performance of the PCR. However, the invention is not intended to be limited to the use of the PCR techniques which are taught in the '202 patent to Mullis, et al.. Since the development of the Mullis, et al. technique, many PCR based assays have been developed which utilize modifications of that technique. These modifications are well-known in the art and will not, therefore, be described in detail here. However, for the purpose of illustrating the scope of the art in this field, several of these modifications are described as follows.

A PCR technique which provides an internal amplification standard using a competitor template which differs from the target nucleic acid in sequence and size is described in *Proc. Natl. Acad. Sci. USA* (1990) 87:2725–2729 (Gilliland, et al., authors). Another technique for performing "competitive" PCR which utilizes templates which differ in sequence but not in size is described in *Nuc. Acids. Res.*, 21:3469–3472, (1993), (Kohsaka, et al., authors). This technique is a particularly preferred technique for its use of enzyme-linked immunoabsorbent assay (ELISA) technology to analyze the amplified nucleic acid(s). A noncompetitive PCR technique which utilizes site-specific oligonucleotides to detect mutations or polymorphisims in genes which may also be applied to the method of the invention is described in *Proc. Natl. Acad. Sci. USA* (1989) 86:6230–6234 (Saiki, et al., authors). Each of these techniques has the advantage of utilizing hybridization probes which assist in eliminating false positive results derived from any nonspecific amplification which may occur during the PCR.

For further background, those skilled in the art may wish to refer to Innis, et al., "Optimization of PCR's", PCR Protocols: A Guide to Methods and Applications (Acad. Press, 1990). This publication summarizes techniques to influence the specificity, fidelity and yield of the desired PCR products.

Oligonucleotide primers (at least one primer pair) are selected which will specifically hybridize to a small stretch of base pairs on either side (i.e., 5' and 3') of the MTAse target polynucleotide (i.e., "flanking sequences"). Those skilled in the art will readily be able to select suitable primers without undue experimentation based on the polynucleotide sequence information set forth in the Sequence Listing appended hereto as SEQ. ID. No. 1 and in FIG. 1.

For primer design, it is important that the primers do not contain complementary bases such that they could hybridize with themselves. To eliminate amplification of any contaminating material which may be present in the sample, primers are preferably designed to span exons (which, for the MTAse gene, are underlined in FIG. 1).

As noted above, it may not be necessary to utilize the chain reaction in this polymerization step in order to adequately amplify the nucleic acids in the sample. For example, where the technique described by Kohsaka, et al., supra is utilized so the polymerization step is performed on solid phase support means and is followed by hybridization with target polynucleotide specific probes, the sensitivity of the assay will be such that a single polymerization of the target polynucleotide may be all that is necessary.

Once the amplification step is complete, the PCR products are assayed to determine thereby whether the gene to encode MTAse is present in the sample. Preferably, the double-stranded PCR products will be bound to the solid phase so their strands may be separated by denaturation, thereby allowing sequence-specific probes to hybridize to the bound antisense strand of the PCR product to detect the gene substantially as described in Kohsaka, et al., supra. Alteratively, the PCR products will be removed from the reaction environment and separated from the amplification mixture prior to the addition of probes for hybridization to the double-stranded PCR products. In this latter approach, the PCR products are separated from the amplification mixture according to methods known in the art with regard to the particular method chosen for detection; e.g., by gel exclusion, electrophoresis or affinity chromatography.

Detection of the amplified product may be achieved by using hybridization probes which are stably associated with a detectable label. A label is a substance which can be covalently attached to or firmly associated with a nucleic acid probe which will result in the ability to detect the probe. For example, a level may be a radioisotope, an enzyme substrate or inhibitor, an enzyme, a radiopaque substance (including colloidal metals), a fluorescors, a chemiluminescent molecule, liposomes containing any of the above labels, or a specific binding pair member. A suitable label will not lose the quality responsible for detectability during amplification.

Those skilled in the diagnostic art will be familiar with suitable detectable labels for use in in vitro detection assays. For example, suitable radioisotopes for in vitro use include $^3H$, $^{125}I$, $^{131}I$, $^{32}P$, $^{14}C$, $^{35}S$. Amplified fragments labeled by means of a radioisotope may be detected directly by gamma counter or by densitometry of autoradiographs, by Southern blotting of the amplified fragments combined with densitometry. Examples of suitable chemiluminescent molecules are acridines or luminol. Target sequences hybridized with probes derivatized with acridium ester are protected from hydrolysis by intercalation. Examples of suitable fluorescers are fluorescein, phycobiliprotein, rare earth chelates, dansyl or rhodamine.

Examples of suitable enzyme substrates or inhibitors are compounds which will specifically bind to horseradish peroxidase, glucose oxidase, glucose-6-phosphate dehydrogenase, β-galactosidase, pyruvate kinase or alkaline phosphatase acetylcholinesterase. Examples of radiopaque substance are colloidal gold or magnetic particles.

A specific binding pair comprises two different molecules, wherein one of the molecules has an area on its surface or in a cavity which specifically binds to a particular spatial and polar organization of another molecule. The members of the specific binding pair are often referred to as a ligand and receptor or ligand and anti-ligand. For example, if the receptor is an antibody the ligand is the corresponding antigen. Other specific binding pairs include hormonereceptor pairs, enzyme substrate pairs, biotin-avidin pairs and glycoprotein-receptor pairs. Included are fragments and portions of specific binding pairs which retain binding specificity, such a fragments of immunoglobulins, including Fab fragments and the like. The antibodies can be either monoclonal or polyclonal. If a member of a specific binding pair is used as a label, the preferred separation procedure will involve affinity chromatography.

If no amplified product can be detected in the assay described above, this is indicative of MTAse deficiency in the cells present in the sample. Because normal (i.e., nonmalignant) cells will always be expected to have MTAse encoding gene present in detectable quantities (even with loss of one allele), a finding that cells lack an MTAse encoding gene (i.e., have a homozygous deletion of the gene) indicates that the cells assayed lack both catalytically active and catalytically inactive MTAse.

However, where desired, the sample can be prescreened for MTAse catalytic activity using the method described by Seidenfeld, et al., *Biochem. Biophys. Res. Commun.*, 95:1861–1866 (1980); see also, Example I, infra). The inventive assay will then be used to determine whether the gene encoding MTAse is present in cells in the sample. The sample may also be tested for the presence of catalytically active or inactive protein for the purpose of screening out cellular contaminants in the sample to be assayed; i.e., nonmalignant cells. A suitable immunoassay for alternative use in this regard (i.e., in lieu of the hybridization assay) is described in Nobori, et al., *Cancer Res.* 53:1098–1101 (1991) and in co-pending, commonly assigned U.S. patent application Ser. No. 08/177,855 filed on Dec. 29, 1993, the disclosure of which has been incorporated herein.

C. MTAse Deficient Cells

Using the assay techniques described above, the following human primary tumors have been determined to be MTAse deficient. It will be understood that this list is representative, but not exhaustive, of the cancer types which may be determined to be MTAse deficient using the assay methods described.

Acute lymphoblastic leukemias (approximately 80% occurrence)

Gliomas (approximately 67% occurrence)

Non-small cell lung cancers (approximately 18% occurrence)

Urothelial tumors (e.g., bladder cancer; incidence varies with tumor type)

Based on these data, MTAse deficiency should be strongly suspected of patients suffering from these conditions. Thus, cell samples from such patients should be routinely assayed for MTAse deficiency to determine whether the patient would be likely to benefit from the therapeutic method of the invention.

Cell samples from other cancer patients should be assayed for MTAse deficiency as clinically indicated. For reference, primary tumor samples from patients suffering from the following conditions have not been found to be MTAse deficient (i.e., the cancers are "MTAse competent"):

Breast cancer

Colon cancer

Head and Neck cancer

Melanoma

Renal cancer

Adult non-lymphoblastic leukemias

Certain acute leukemias (adult and juvenile)

Clinical trials have been conducted using L-alanosine to treat the above-listed MTAse competent cancers, with no appreciable success.

II. METHOD FOR TREATMENT OF MTAse DEFICIENT CELLS

A. Pharmacology and Toxicity Parameters for L-alanosine

In primates, approximately 75% of L-alanosine is excreted in urine in about 24 hours, primarily as the nucleoside forms of L-alanosinyl-IMP and L-alanosinyl-AICOR. Clearance from plasma after intravenous administration in humans is biphasic, with $t_{1/2}\alpha=14$ minutes and $t_{1/2}\beta=99$ minutes (where "$t_{1/2}$" is the half-life and times (t) are approximate).

In prior clinical trials, toxicity has been dose-limiting, including renal toxicity, stomatitis, esophagitis and, with lesser frequency, myelosuppression, headache, nausea and hypo- or hypertension. Renal toxicity occurred with single bolus dosing above 4 g/m² body weight. Further, two pediatric patients who received higher doses of about 350 mg/m² body weight per day in separate doses suffered liver failure. Stomatitis and esophagitis occurred after multiple bolus dosing. The other observed reactions were patient specific.

One phase II trial utilized continuous infusion at a dose of about 125 mg/m² body weight for 5 days in adults suffering from acute non-lymphoblastic leukemia. The dose limiting toxicity was mucositis.

B. Administration of ASS Inhibitors to a Host

Mammalian hosts (e.g., humans) suffering from cancers determined to be MTAse deficient according to the MTAse deficiency assay of the invention are treated with therapeutically effective dosages of an ASS inhibitor such as L-alanosine, L-alanosinyl-AICOR or hadacidin, preferably the former. In this respect, a "therapeutically effective dosage" is one which produces an objective tumor response in evaluable patients, where tumor response is a cessation or regression in growth determined against clinically accepted standards (see, e.g., Eagan, et al., *Cancer,* 44:1125–1128, 1979 [the disclosure of which is incorporated herein by this reference] and the publicly available reports of parameters applied (essentially per Eagan, et al.) in the clinical trials performed under IND#14,247 (Food and Drug Administration)). With reference to these standards, determination of therapeutically effective dosages for ASS inhibitors to be used in the invention for depletion of intracellular AMP may be readily made by those of ordinary skill in the oncological art.

In general, daily administration or continuous infusion of ASS inhibitors at dosages less than those known to produce toxicities will be the preferred therapeutic protocol to enhance the anti-metabolite activity of the drugs. Due to the unique sensitivity of MTAse deficient cells to this method of treatment, it can be expected that dosages less than those tested in clinical trials of L-alanosine in treatment of MTAse competent cells will be required, thus reducing toxicity to non-proliferating cells.

Non-malignant, MTAse competent cells may also be protected from any effect of exposure to ASS inhibitors through administration of MTA or a suitable substrate analogue for use in adenine synthesis. Suitable compounds for use in this regard include MTA, 2'-5' dideoxyadenosine, 5'-deoxyadenosine, 2'-deoxy-5-deoxy-5'methylthioadenosine (see, e.g., Example II). It will be appreciated, however, that MTAse competent cells are capable of producing adenine from metabolism of methylthioadenosine for replenishment of the AMP cellular pool and therefore would not be expected to be depleted of AMP to the same extent as MTAse deficient cells.

The invention having been fully described, its practice is illustrated by the examples set forth below. It will be understood, however, that the examples do not limit the scope of the invention, which is defined by the appended claims. Standard abbreviations are used throughout the Examples, such as "ml" for milliliter, "h" for hour and "mg" for milligram.

EXAMPLE I

IN VIVO EFFECT OF L-ALANOSINE ON MTAse DEFICIENT AND MTAse COMPETENT HUMAN TUMOR XENOGRAFTS AFTER CONTINUOUS INFUSION

To evaluate the in vivo effect of L-alanosine on known human MTAse deficient tumors after continuous infusion, and to compare that effect to the drug's effect on known human MTAse competent tumors, $2 \times 10^6$ MTAse deficient H292 NSCLC cells and MTAse competent Calu-6 tumor cells (in 0.3 ml with 50% MATRIGEL™ carrier), were injected into the right and left flank, respectively, of 8 Balb/C athymic nude mice. MATRIGEL™ initially forms a solid matrix in vivo that was measured in each mouse on the first day of infusion for a control tumor size (which is resorbed over a 14-day period). For further comparison, $10^7$ CEM T-ALL (MTAse deficient acute lymphoblastic leukemia) cells in 50% MATRIGEL™ carrier were injected into the right flank of 8 other nude mice. Many of the cells were obtained from commercially available cell lines from the ATCC sold under, respectively, ATCC Accession Nos. CRL-1848 and HTB-56.

The following day, 4 mice with bilateral NSCLC and 4 with T-ALL inocula were implanted subcutaneously with ALZET™ 1007D osmotic infusion pumps in the back at a distance from tumor cell inoculation sites. The pumps had been filed with L-alanosine at a concentration calculated to deliver 60 mg/kg daily by continuous infusion. Because no toxicity was evident after 7 days at the 60 mg/kg dosage, the pumps were removed and replaced with pumps containing L-alanosine for delivery of 90 mg/kg per day for an additional 7 days.

Figure 2:
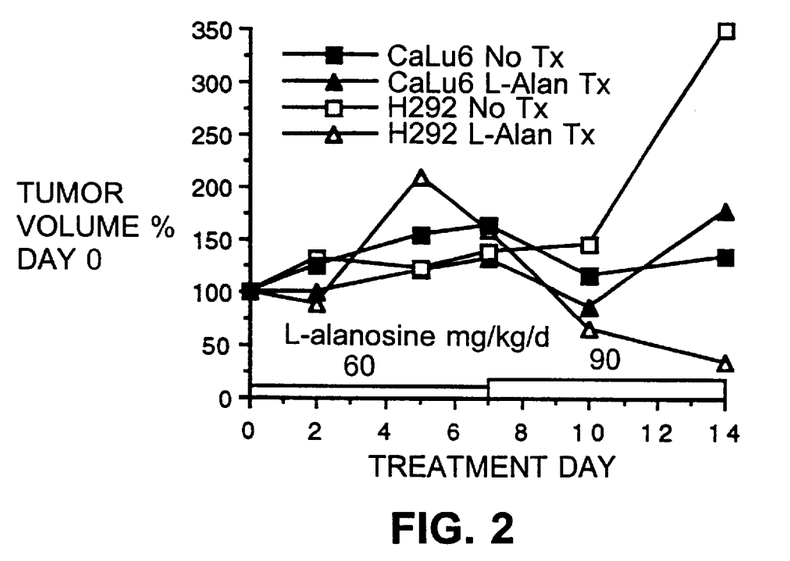
FIG. 2 is a graph depicting the in vivo effect of L-alanosine after continuous infusion on established human MTAse competent and MTAse deficient non-small cell lung cancer xenograft tumors in nude mice.
Figure 3:
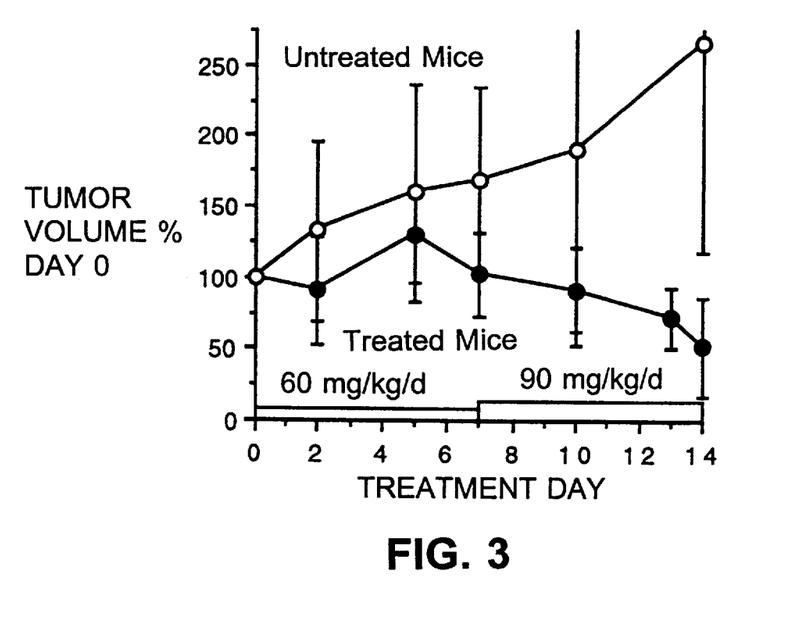
FIG. 3 is a graph depicting the in vivo effect of L-alanosine after continuous infusion on established human MTAse deficient acute lymphoblastic leukemia xenograft tumors in nude mice.

As shown in FIG. 2 and FIG. 3, the administered L-alanosine caused the shrinkage of established MTAse deficient NSCLC ("H292 L-alan Tx"; FIG. 2) and T-ALL ("Treated mice"; FIG. 3) xenograft inocula in immunodeficient murine hosts and prevented the growth of recent MTAse-deficient NSCLC or T-ALL xenograft inocula in immunodeficient murine hosts as compared to treated MTAse competent NSCLC cells and untreated MTAse-deficient cells. In particular, established MTAse competent tumors grew rapidly despite L-alanosine, as did untreated MTAP-deficient NSCLC or T-ALL xenografts.

EXAMPLE II

PROTECTION OF MTAse COMPETENT HEALTHY CELLS WITH MTAse SUBSTRATES

Figure 4:
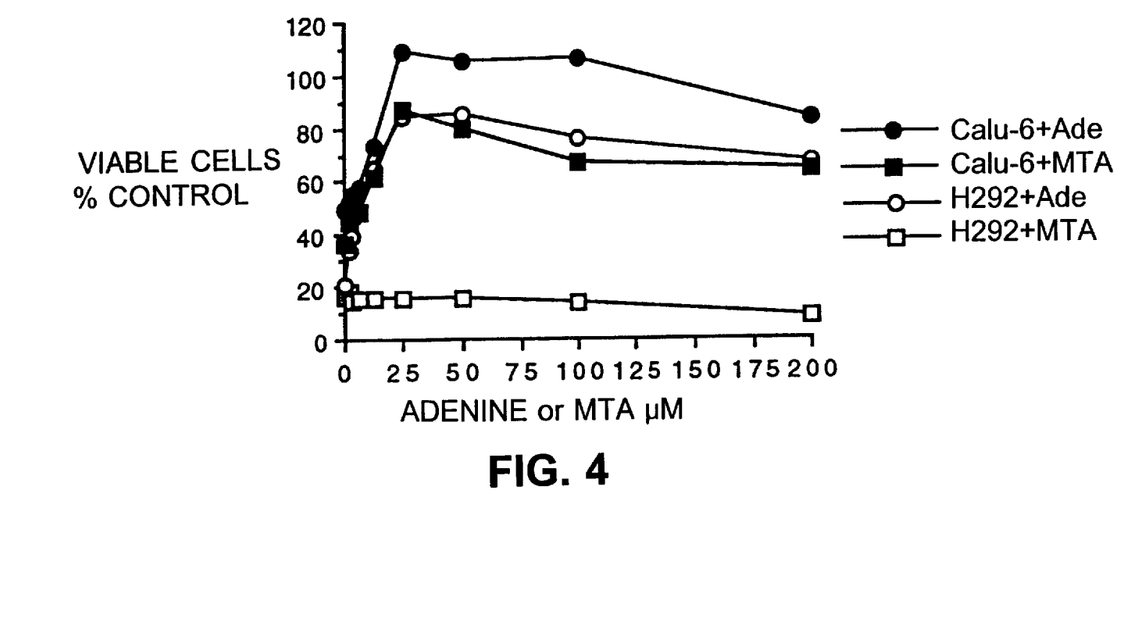

The selective inability of MTAse deficient NSCLC cells to proliferate in the presence of L-alanosine (at 40 $\mu$M) despite the addition to each culture of the MTAse substrate methylthioadenosine(MTA) was confirmed in a comparison of two cell lines, MTAse competent Calu-6 and MTAse deficient H292 (FIG. 4). Control cultures containing adenine (tAde) proliferate despite L-alanosine, confirming that the selective toxicity is due to a failure of MTAse-deficient cells to metabolize MTA to adenine.

Figure 5A:
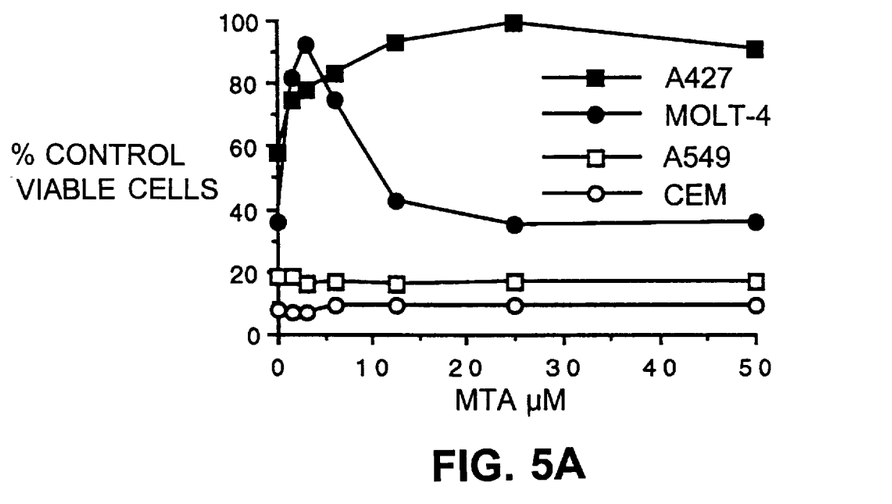
Figure 5B:
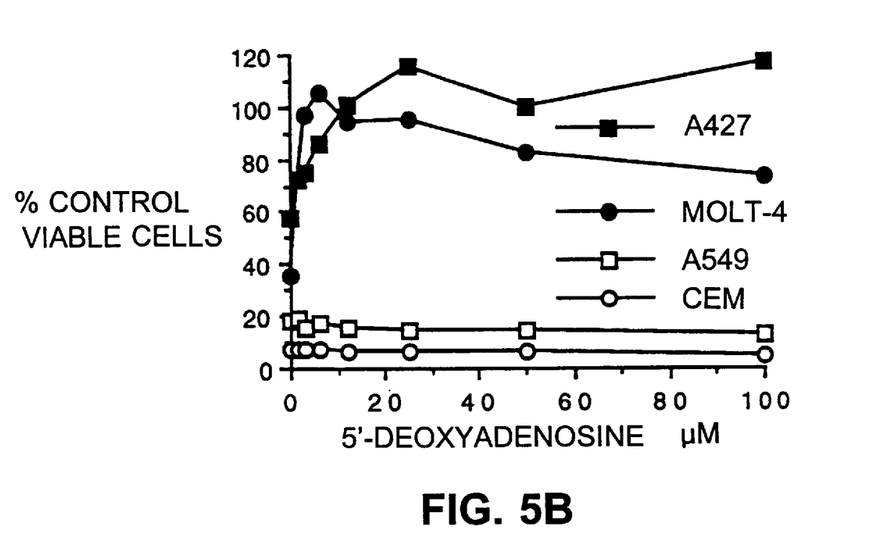

For further comparison, the addition of MTA or the MTA substrate analogue 5'-deoxyadenosine resulted in growth restoration only for MTAse competent A427 cells and MOLT-4 cells, whereas MTAse deficient A549 and CEM cells remained growth inhibited (FIG. 5A and B). Because MTA is a feedback inhibitor of spermine synthetase, some cell lines such as MOLT-4 are inhibited by high concentrations. This results in a biphasic growth restoration curve with increasing MTA concentration (FIG. 5A).

EXAMPLE III

CLONING AND PARTIAL CHARACTERIZATION OF THE MTAse GENOMIC CLONE

A genomic clone of human MTAse was isolated as follows. A cosmid gene library constructed from human placenta DNA (Clontech) was screened using MTAse cDNA gene probe, the Not I/EcoRi fragment from subclone MTAP-7. Transformed E. coli cells from the library are plated on LB plates containing ampicillin (50 mg/l) with a colony density of $1-2 \times 10^4/135 \times 15$ mm plate.

The following procedures were performed. From half a million colonies, a single positive colony designated as MTAP-10 was isolated and partially characterized by PCR analysis and by direct sequencing. Two primers, a sense oligonucleotide located 120 bp upstream of the stop codon and an anti-sense oligonucleotide located 20 bp downstream of the stop codon were synthesized and used for PCR analysis. PCR was performed for 25 cycles, each cycle consisting of denaturation (92° C., 1 min), annealing (55° C., 2 min) and extension (72° C., 5 min). The PCR products were separated on a 0.8% agarose gel.

The location of exons identified to date in the MTAse gene using the above-described technique is depicted in FIG. 1 by underlining.

EXAMPLE IV

APPLICATION OF MTAse SEQUENCE-SPECIFIC OLIGONUCLEOTIDES TO MALIGNANT CELL LINES TO DETECT THE PRESENCE OR ABSENCE OF MTAse THEREIN

To test the usefulness of oligonucleotide probes developed from the MTAse genomic clone identified as described in Example IV (SEQ.ID.No. 1), PCR was applied to several human lung cancer cell lines which were known to contain MTAse competent(Calu-6; ATCC Designation No. HTB-56) and deficient cells (A549; ATCC Designation No. CCL-185). Genomic DNA was isolated as described in Example III and 1 microgram thereof was used for PCR.

Amplification was performed for 40 cycles as described above, with each cycle consisting of denaturation (92° C., 1 min) annealing (55° C., 1 min), and extension (72° C., ½ min). The PCR products were analyzed on a 1.5% agarose gel. No MTAse was detected in cell lines which were known to be MTAse deficient, while MTAse was detected in the MTAse competent cell lines.

EXAMPLE V

L-ALANOSINE INHIBITION OF MTAP-DEFICIENT TUMORS AFTER DAILY INJECTION INTO NUDE MICE WITH ESTABLISHED TUMOR XENOGRAFTS $10^7$ A549 or A427 NSCLC cells were injected subcutaneously into 6-week old Balb/c athymic nude mice. When tumors had reached approximately 0.4 cm diameter, treatment was begun with L-alanosine or saline by intraperitoneal injection every 12 hours.

Figure 7:
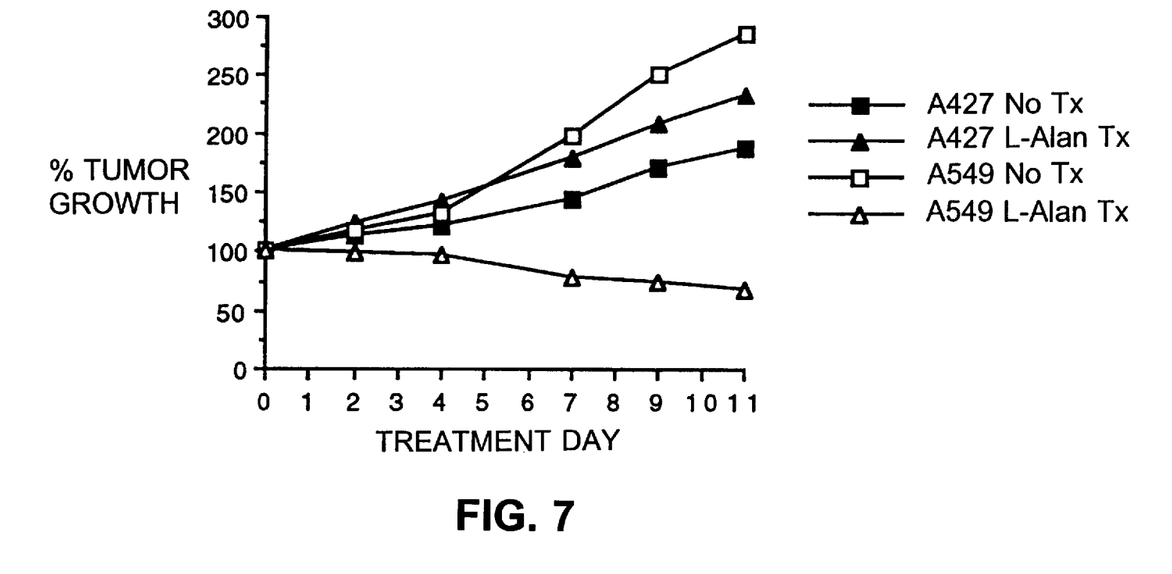
FIG. 7 is a graph depicting the in vivo effect of L-alanosine after daily injection on established human MTAse deficient non-small cell lung cancer xenograft tumors in nude mice.

Mice received 15 mg/kg per injection for 7 days then 22.5 mg/kg for 5 days. Tumor size was measured as the product of perpendicular diameters. The results for treated (n=6 [sample size] for each cell type) vs. control (n=4 [sample size] for each cell type) mice are shown in FIG. 7.

No toxicity was evident at either dosing level tested (mice had stable weights throughout testing). L-alanosine administered by twice daily bolus injection caused a decrease in the size of well-established MTAP-deficient tumors, but had no effect on the growth of MTAP-positive cells.

SUMMARY OF SEQUENCES

SEQUENCE ID. NO. 1 is the genomic clone for methylthioadenosine phosphorylase (MTAse).

We claim:

1. A method for inhibiting the activity of adenyl succinate synthetase (ASS) in methythioadenosine phosphorylase (MTAse) deficient cells comprising:
   (a) determining that a population of cells obtained from a mammalian host is MTAse deficient; and,
   (b) administering a therapeutically effective amount of an ASS inhibitory agent to the host, wherein said contact has the effect of depleting MTAse deficient host cells of adenosine 5'-monophosphate.

2. The method according to claim 1 wherein step (a) is performed by:
   (a) obtaining an assayable sample of cells which are suspected of being MTAse deficient;
   (b) adding oligonucleotide probes which will specifically hybridize to any of the MTAse encoding nucleic acid present in the sample to the sample under conditions which will allow the probes to detectably hybridize to any such nucleic acid present in the sample; and,
   (c) detecting whether MTAse encoding nucleic acid is present in the sample, wherein the presence of said nucleic acid is indicative of the presence of MTAse protein in the sample of cells.

3. The method according to claim 1 wherein the ASS inhibitory agent is L-alanosine.

4. The method according to claim 1 wherein the host is a human.

5. The method according to claim 1 wherein the MTAse deficient host cells are primary tumor cells selected from the group consisting of non-small cell lung cancer cells, acute lymphoblastic leukemia cells, glioma cells and urothelial tumor cells.

6. The method according to claim 1 wherein the ASS inhibitory agent is administered to the host by infusion or in single doses.

7. The method according to claim 1 wherein a substrate for intracellular production of AMP is administered to the host after treatment of the host according to step (b).

8. A method for inhibiting the activity of adenylsuccinate synthetase (ASS) in cells of a mammalian host, wherein the cells are known to be methythioadenosine phosphorylase (MTAse) deficient; the method comprising administering a therapeutically effective amount of an ASS inhibitory agent to the host, wherein said contact has the effect of depleting MTAse deficient host cells of adenosine 5'-monophosphate.

9. The method according to claim 8 wherein the ASS inhibitory agent is L-alanosine.

10. The method according to claim 8 wherein the host is a human.

11. The method according to claim 8 wherein the MTAse deficient host cells are primary tumor cells selected from the group consisting of non-small cell lung cancer cells, acute lymphoblastic leukemia cells and glioma cells.

12. The method according to claim 8 wherein the ASS inhibitory agent is administered to the host by infusion or in single doses.

13. The method according to claim 8 wherein a substrate for intracellular production of AMP is administered to the host after administration of the ASS inhibitory agent to the host.

* * * * *

UNITED STATES PATENT AND TRADEMARK OFFICE
CERTIFICATE OF CORRECTION

PATENT NO : 5,840,505
DATED : November 24, 1998
INVENTOR(S): Carrera et al.

It is certified that error appears in the above-identified patent and that said Letters Patent is hereby corrected as shown below:

Column 1, line 11, insert after the title please insert --This invention was made with Government support under Grant No. CA54892, awarded by the National Institutes of Health.--

Signed and Sealed this

Seventh Day of December, 1999

Attest:

Q. TODD DICKINSON

Attesting Officer

Acting Commissioner of Patents and Trademarks